United States Patent
Williams et al.

(10) Patent No.: US 6,790,436 B2
(45) Date of Patent: Sep. 14, 2004

(54) GEL AIR FRESHENER

(75) Inventors: Virgil A. G. Williams, Leonardo, NJ (US); Craig M. Stumpf, Branchburg, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 18 days.

(21) Appl. No.: 10/015,367

(22) Filed: Dec. 13, 2001

(65) Prior Publication Data
US 2003/0113288 A1 Jun. 19, 2003

(51) Int. Cl.$^7$ .............................. A61L 9/04; A61L 9/12; A61K 9/14; A01N 25/00
(52) U.S. Cl. ..................... 424/76.3; 424/484; 424/488; 424/405; 424/76.2
(58) Field of Search .................................. 424/484, 488, 424/405, 76.3, 9.5, 76.2, 4.5

(56) References Cited

U.S. PATENT DOCUMENTS

| | | | |
|---|---|---|---|
| 5,679,334 A | * | 10/1997 | Semoff et al. .............. 424/76.4 |
| 5,698,188 A | | 12/1997 | Evans |
| 6,071,506 A | | 6/2000 | Semoff II, et al. |
| 6,171,560 B1 | * | 1/2001 | Pesu et al. ................... 422/305 |
| 6,214,063 B1 | * | 4/2001 | DeStefano et al. ........... 44/275 |
| 6,294,162 B1 | | 9/2001 | Semoff III, et al. |
| 6,309,715 B1 | | 10/2001 | Lindauer et al. |

FOREIGN PATENT DOCUMENTS

| | | |
|---|---|---|
| EP | 0 761 240 A1 | 3/1997 |
| WO | WO 00/73408 | 12/2000 |
| WO | WO 01/87361 A2 | 5/2001 |

* cited by examiner

*Primary Examiner*—Blessing M. Fubara

(57) ABSTRACT

Described is a substantially rigid aqueous clear gel matrix air freshener article having included therein one or more gel matrix icons, the dimensions of which, on use of the article, decrease in proportion to the dimensions of the body of the air freshener article in which the icons are suspended and imbedded. The article contains water; gel matrix material which can be a hydrolyzed protein gel material such as gelatin or a polysaccharide gel material such as gellan gum; a system-compatible air freshener fragrance composition contained in one or more of the icons and/or contained in the gel matrix air freshener body; and a surfactant contained in the body.

18 Claims, No Drawings

GEL AIR FRESHENER

FIELD OF THE INVENTION

This invention relates to substantially rigid, clear gel matrix air freshener articles having included therein one or more gel matrix icons, the dimensions of which decrease in proportion to the dimensions of the body of the air freshener article, in which the icons are imbedded, on use thereof, as a result of water and fragrance emission therefrom into the environment surrounding the articles.

BACKGROUND OF THE INVENTION

Clear candles with included icons that appear opaque and visually distinct from the clear matrix of the candle are highly desirable and are known in the prior art. Such candles fabricated using non-aqueous ester-terminated polyamide systems are disclosed in Berger et al., PCT Application WO 00/73408 A1, as well as DeStefano et al., U.S. Pat. No. 6,214,063. However, icon-containing systems which provide desirable clear appearances, such as those disclosed for clear candles, are not available or known for rigid aqueous gel matrix air freshener systems. Thus, there exists a need for substantially rigid aqueous gel matrix-containing air freshener articles which include one or more icons imbedded therein which are visibly detectable from without the air freshener article at visible wavelengths. For such articles to be useful, as (i) water and (ii) air freshener fragrance composition is emitted from the air freshener article on use thereof, the dimensions of each of the icons imbedded in the air freshener gel matrix body must, on use of the air freshener, decrease in proportion to the dimensions of the air freshener gel matrix body in order (i) to maintain its physical integrity and (ii) to achieve a continuously aesthetically pleasing appearance of the article.

The prior art does disclose substantially rigid clear aqueous and non-aqueous polymeric air freshener articles which contain visibly detectable icons, for example, icons which are botanicals, as disclosed in U.S. Pat. Nos. 5,679,334; 6,071,506, 6,294,162 and 6,309,715, all hereby incorporated by reference as if set forth in their entirety. However, such prior art aqueous and non-aqueous polymeric icon-containing air freshener articles do not have the unexpected and non-obvious advantages that the aqueous gel matrix icon-containing articles of our invention have. Indeed, the prior art does not specifically or implicitly teach the advantages of icon construction from gel matrix materials and use of such icons in conjunction with substantially rigid clear gel matrix aqueous air freshener articles.

SUMMARY OF THE INVENTION

Our invention provides a substantially rigid aqueous gel air freshener article having included in the gel matrix air freshener body thereof, one or more gel matrix icons that decrease in volume in proportion to volume of the air freshener body gel matrix on use of the air freshener article.

More particularly, our invention provides a substantially rigid aqueous gel air freshener article comprising:

(a) an air freshener body having a volume $V_o$ which decreases on use of said air freshener article whereby, as a result of emission of at least water and, optionally, to a substantially lesser extent fragrance, therefrom, the rate of change of the air freshener body volume with respect to time, $dV_o/d\theta<0$, comprising water, a surfactant, a clear gel matrix material which is, in the alternative, one or both of a polysaccharide gel matrix material and/or a hydrolyzed protein gel matrix material, and, optionally, a system-compatible air freshening fragrance composition;

(b) fully imbedded within said air freshener body, one or more gel matrix icons which are each visibly distinct over the range of visible wavelengths when contained within said air freshener, the total volume of which is $V_I$ which decreases on use of said air freshener article whereby, as a result of the emission of at least water and, optionally, to a substantially lesser extent;

(c) fragrances, therefrom, the rate of change of the icon volume with respect to time, $dV_I/d\theta<0$, each of which icon comprises (i) water, (ii) a clear gel matrix material which is, in the alternative, either or both of a polysaccharide gel matrix material and/or a hydrolyzed protein gel matrix material, (iii) optionally, a system-compatible air freshening fragrance composition and (iv), optionally, a surfactant, with the proviso that the system-compatible air freshening fragrance compositions are present in at least one of said icons, or in said air freshener body, or in at least one of said icons and in said air freshener body, the volume fraction of said icons in said air freshener article being $\phi=V_I/(V_I+V_o)$, wherein $0.01 \leq \phi \leq 0.90$, the physical and chemical properties of each of said icons and said air freshener body being such that on use of said air freshener article, (i) the rate of volumetric reduction of each of said icons as a result of fragrance emission, if any, and water emission therefrom with respect to the volumetric reduction of the air freshener body which envelops said icons as a result of fragrance emission, if any, and water emission therefrom is a constant, according to the equations: $\partial V_I/\partial V_o=\phi/(1-\phi)$ and $\partial^2 V_I/\partial V_o^2=0$, (ii) the integrity of the fragrance compositions emitted from said air freshener body and said icons is maintained and (iii) the distinguishing visibility of the icons in said air freshener from without said air freshener, at visible wavelengths, is maintained.

Furthermore, the substantially rigid gel matrix air freshener article of our invention can have a gel matrix air freshener body which additionally comprises at least one additive such as an antimicrobial agent; an anti-oxidant; a non-gelling hydrocolloid; a chelating agent; a $C_2-C_6$ alkylene glycol; a lower alkanol; and a $C_2-C_6$ (mono- or di-) alkylene glycol-$C_2-C_4$ alkyl ether.

In addition, the substantially rigid gel matrix air freshener article of our invention can include icons which additionally comprise at least one additive such as an opacifying agent; an anti-microbial agent; an anti-oxidant; a non-gelling hydrocolloid; a chelating agent; a $C_2-C_6$ alkylene glycol; a lower alkanol; and a $C_2-C_6$ (mono- or di-)alkylene glycol mono-$C_2-C_4$ alkyl ether.

The substantially rigid gel matrix air freshener article of our invention may be fully encompassed by a clear substantially solid or semi-solid microporous boundary surface which surface permits passage of water molecules and air freshener fragrance composition component molecules therethrough on the use of the article.

In addition, the substantially rigid gel matrix air freshener article of our invention may be externally supported by means of an external support comprising a solid base having vertically-disposed solid sidewalls extending therefrom such as a vertically disposed cylindrical glass jar open at the top.

Our invention also provides a process for preparing such air fresheners comprising the steps of:

(a) providing at least one gel-matrix icon;
(b) cooling the icon to a temperature below the solidification point thereof;

(c) providing the gel matrix air freshener body in the liquid phase; and (d) immersing totally the solidified icon in the gel matrix air freshener body.

In one embodiment of the invention, both the gel matrix icons and the gel matrix air freshener body are prepared from water; gel matrix material which is gellan gum; the antimicrobial materials, methylchloroisothiazolinone and methylisothiazolineone; propylene glycol; ethyl alcohol; the surfactant, nonoxynol-15(o(hydroxy(ethoxy)$_{15}$)) nonylphenyl ether or PEG-15 nonylphenyl ether, in the case of the gel matrix air freshener article body or nonoxynol-4, PEG-4 nonylphenyl ether, in the case of the gel matrix air freshener article icon; the chelating agent, tri-potassium citrate; and system-compatible air freshener fragrance, the components of which have an average $Clog_{10}P$ of 2.5 in the case of the gel matrix air freshener article body and the components of which have an average $Clog_{10}P$ of 4.5 in the case of the gel matrix air freshener article icon, where P is the n-octanol/water partition coefficient for each of the components of the fragrance. Pigment is added to the icon material in an amount effective for making the icon material opaque and then the material is molded to form icons. In a preferred embodiment, the icons are placed in ajar and solidified or even frozen. Hot gel matrix material is poured over the frozen icons to provide a gel air freshener having included icons that, on use of the gel matrix air freshener article, decrease in dimensions and volume in proportion to the dimensions and volume of the gel matrix air freshener article.

It is thus an object of the invention to provide a novel gel matrix clear air freshener article.

It is a further object of the invention to provide a novel gel matrix clear air freshener article having included in the gel matrix air freshener body, gel matrix icons.

It is a still further object of the invention to provide a novel gel matrix clear air freshener article having included in the gel matrix air freshener body, gel matrix icons that, on use of the article, decrease in volume in proportion to the volume of the gel matrix air freshener body.

Still other objects and advantages of the invention will in part be obvious and will in part be apparent from the following detailed description and the appended claims.

DETAILED DESCRIPTION OF THE INVENTION

The substantially rigid gel matrix clear air freshener provided in accordance with our invention has included therein one or more visibly detectable gel matrix icons the dimensions and volume of which decrease in proportion to the dimensions and volume of the gel matrix air freshener body surrounding the icons and in which the icons are imbedded, on use of the air freshener article. As used herein the word icon is also understood to include icon plural, that is one or more icons.

The substantially rigid gel matrix air freshener articles contemplated by our invention, prior to use, are intended to be fully enclosed by an air tight packaging material whereby water molecules and fragrance composition molecules that are contained in the gel matrix icons and in the gel matrix air freshener body can not be transported outwardly from the article of our invention to the environment surrounding the article. On removal of such air tight packaging material from around the gel-matrix air freshener article of our invention, removing the gel matrix air freshener article of our invention from the surrounding air tight packaging material, the gel matrix air freshener article of our invention is, at that point in time, "in use" in accordance with the practice of our invention.

The gel matrix air freshener article of our invention preferably contains, in the gel matrix air freshener body and/or in the gel matrix icon, a clear gel matrix material which is a polysaccharide which may be at least one of a gellan gum, e.g. KELCOGEL® gum trademark of the Monsanto Company of St. Louis, Mo., a linear high molecular weight extracellular partially acetylated, partially glycerated anionic polysaccharide, an alkali metal salt of alginic acid, e.g., sodium alginate or potassium alginate; an alkaline earth metal salt of alginic acid, e.g., calcium alginate or magnesium alginate; and/or carageenan.

The air freshener article of our invention may, as an alternative to the gel matrix material which is a polysaccharide, contain in the gel matrix air freshener body and/or in the gel matrix icon a hydrolyzed protein gel matrix material composed of gelatin having an isoelectric point of from about 4 up to about 7, a type 'B' gelatin.

The gel matrix clear air freshener article of our invention preferably contains, in the gel matrix air freshener body, an antimicrobial agent, a chelating agent, a lower alkanol, a non-gelling hydrocolloid and a $C_2$–$C_6$ alkylene glycol or a $C_2$–$C_6$ (mono- or di) alkylene glycol $C_2$–$C_4$ alkyl ether. At least one of the gel matrix icons can also contain an antimicrobial agent, a chelating agent, a lower alkanol, a non-gelling hydrocolloid and a $C_2$–$C_6$ alkylene glycol or a $C_2$–$C_6$ (mono- or di-) alkylene glycol $C_2$–$C_4$ alkyl ether. The antimicrobial agent is preferably one or more of potassium dimethyldithiocarbamate, glutaraldehyde, 2-bromo-2-nitropropane-1,3-diol, o-phenyl phenol, 1-(3-chloroallyl)-3,5,7-triaza-1-azoniaadamantane chloride, N,N'-dimethyl-5,5-dimethoxy-2,4-imidazolidinedione, methylchloroisothiazolinone and/or methylisothiazolinone. The chelating agent is preferably one or more of an alkali metal salt of citric acid, e.g., tri-sodium citrate or tri-potassium citrate; an ammonium salt of citric acid, e.g., ammonium, di-sodium citrate; an alkali metal salt of ethylenediamine tetraacetic acid, e.g., the tri-sodium salt; an ammonium salt of ethylene diamine tetraacetic acid, e.g., the mono-ammonium, di-sodium salt; an alkali metal salt of N-hydroxyethylenediamine triacetic acid, e.g., the tri-sodium salt; an ammonium salt of N-hydroxyethylenediaminetriacetic acid, e.g., the ammonium, di-sodium salt; an alkali metal salt of iminodisuccinic acid, e.g., the di-sodium salt, an ammonium salt of iminodisuccinic acid, e.g., the mono-ammonium, mono-sodium salt; an alkali metal salt of ethylenediamine disuccinic acid, e.g., the di-potassium, di-sodium salt; and an ammonium salt of ethylene diamine disuccinic acid, e.g., the mono-ammonium, di-sodium salt. The $C_2$–$C_6$ alkylene glycol is preferably 1,2-propylene glycol. The lower alkanol is, preferably ethanol. The $C_2$–$C_6$ (mono- or di-) alkylene glycol $C_2$–$C_4$ alkyl ether is preferably dipropylene glycol n-butyl ether. The preferred non-gelling hydrocolloid is one of locust bean gum, guar gum, xanthan gum, starch or carboxymethylcellulose.

The purpose of the presence, in the gel matrix air freshener body and/or icon, of the non-gelling hydrocolloid is as a processing aid for gelling; that is, preventing syneresis and improving clarity in the gel matrix on use of the gel matrix air freshener article of our invention.

As stated herein, an air freshener fragrance composition is included in either the gel matrix air freshener body or in at least one gel matrix icon or in both the gel matrix air freshener body and in at least one gel matrix icon. Where such air freshener fragrance is used, it is used in an amount of between about 0.1% and about 20% by weight of the composition, preferably in an amount between about 1% and about 10% by weight, most preferably in an amount of about 5% by weight.

Preferably, the design of the fragrance employed in the gel matrix air freshener article body should differ from the design of the fragrance employed in the gel matrix air freshener article icon(s) whereby (i) the average "$Clog_{10}P$" for the fragrance components in the gel matrix air freshener article body is about 2.5 and (ii) the average "$Clog_{10}P$" in the gel matrix air freshener article icon(s) is about 4.5 wherein P is the n-octanol/water partition coefficient for each of the fragrance components.

The $log_{10}P$ of many perfume ingredients has been reported; for example, the Pomona 92 database, available from Daylight Chemical Information Systems, Inc. hereafter referred to as "Daylight CIS", Irvine, Calif., contains many, along with citations to the original literature. However, the $log_{10}P$ values are most conveniently calculated by the "CLOGP" program, also available from Daylight CIS. This program also lists experimental $log_{10}P$ values when they are available in the Pomona 92 database. The "calculated $log_{10}P$", hereafter referred to as "$Clog_{10}P$" is determined by the fragment approach of Hansch and Leo cf., A. Leo in Comprehensive Medicinal Chemistry, Vol. 4, C. Hansch, P. G. Sammens, J. B. Taylor and C. A. Ramsden, Eds., p.295, Pergamon Press, 1990. The fragment approach is based on the chemical structure of each perfume ingredient, and takes into account the numbers and types of atoms, the atom connectivity and the chemical bonding. The $Clog_{10}P$ value which are the most reliable and widely used estimates for this physiochemical property, are preferably used instead of the experimental $log_{10}P$ values for the selection of perfume ingredients which are useful in the gel matrix air freshener articles of our invention.

More specifically, the gel matrix air freshener article of our invention can contain an air freshening fragrance composition within the gel matrix air freshener body immediately prior to use of the article, that is, for example, when the article is still contained in an air tight packaging material, and the air freshening fragrance composition that would be contained in the gel matrix air freshener body preferably consists essentially of fragrance components each of which has a C $log_{10}P$ of from about 1 up to about 4 wherein P is the octanol/water partition coefficient for each of said fragrance components.

Specific examples of preferred fragrance components useful in the gel matrix air freshener body and the $Clog_{10}P$ of each of these components is as follows:

| Fragrance Component | $Clog_{10}P$ value |
|---|---|
| Benzaldehyde | 1.480 |
| Benzyl acetate | 1.960 |
| Laevo-carvone | 2.083 |
| Geraniol | 2.649 |
| Cis-jasmone | 2.712 |
| β-Phenylethyl alcohol | 1.183 |
| α-Terpineol | 2.569 |
| δ-Nonalactone | 2.760 |
| Dihydromyrcenol | 3.03 |
| δ-Undecalactone | 3.830 |
| Amyl cinnamate | 3.771 |
| Benzophenone | 3.120 |
| α-Irone | 3.820 |
| Nerol | 2.649 |
| 2-Methoxynaphthalene | 3.235 |
| Musk ketone | 3.014 |
| Musk tibetine | 3.831 |
| Myristicin | 3.200 |
| 6-Phenyl heptanol-2 | 3.478 |
| 1-Phenyl hexanol-5 | 3.299 |

-continued

| Fragrance Component | $Clog_{10}P$ value |
|---|---|
| α-Santalol | 3.800 |
| Iso-eugenol | 2.547 |
| Linalyl acetate | 3.500 |
| Eugenol | 2.307 |

As stated herein, the gel matrix air freshener article of our invention can contains an air freshening fragrance composition in one or more of the gel matrix icons contained in the gel matrix air freshener body prior to use of the article, and the air freshening fragrance composition preferably consists essentially of fragrance components, each of which has a $Clog_{10}P$ of from about 1 up to about 8 wherein P is the octanol/water partition coefficient for each of said fragrance components.

Specific examples of preferred fragrance components useful in the gel matrix air freshener icons and their respective $Clog_{10}P$ values are as follows:

| Fragrance Component | $Clog_{10}P$ value |
|---|---|
| Amyl salicylate | 4.601 |
| Benzyl salicylate | 4.383 |
| β-Caryophyllene | 6.333 |
| Cedrol | 4.530 |
| Cedryl acetate | 5.436 |
| Cedryl formate | 5.070 |
| Cyclohexyl salicylate | 5.265 |
| γ-Dodecalactone | 4.359 |
| Ethyl undecylenate | 4.888 |
| Geranyl anthranilate | 4.216 |
| α-Irone | 3.820 |
| Linalyl benzoate | 5.233 |
| Patchouli alcohol | 4.530 |
| 5-Acetyl-1,1,2,3,3,6-hexamethyl indane | 5.977 |
| Cyclopentadecanolide | 6.246 |
| d-Limonene | 4.232 |
| Cis-p-t-butylcyclohexyl acetate | 4.019 |
| Amyl cinnamic aldehyde | 4.324 |
| Linalyl benzoate | 5.233 |

In the gel matrix air freshener article of our invention, when at least one of the gel matrix icons contained in the gel matrix air freshener body contains an air freshening fragrance composition prior to use of the article, the icon containing the air freshener fragrance composition may also contain a surfactant having a hydrophile/lipophile balance of less than about 10.

In the gel matrix air freshener body of the gel matrix air freshener article of our invention, the surfactant has a hydrophile/lipophile balance in the range of from about 10 up to about 30. Preferred surfactants are poly ($C_2$–$C_4$ alkylene glycol)$_{6-30}$ mono([$C_8$–$C_{10}$ alkyl]phenyl)ethers, e.g., nonoxynol-15, HLB=15; 1,ω-poly $C_2$–$C_4$alkylene glycols, e.g., POLOXAMER-108, HLB=30, a methyl oxirane polymer, CAS #9003-11-6; poly $C_2$–$C_4$ alkylene glycol mono-$C_{10}$–$C_{20}$ alkanoic acid esters, e.g., PEG-40 stearate; poly $C_2$–$C_4$ alkylene glycol sorbitan mono-$C_{10}$–$C_{20}$ alkanoic acid esters,e.g., POLYSORBATE-20; poly $C_2$–$C_4$ alkylene glycol tallow amines, e.g., SURFONIC T-50, HLB=17.8, Huntsman Petrochemical Corp., Salt Lake City, Utah; poly $C_2$–$C_4$ alkylene glycol esters of tall oil fatty acids, e.g., SURFONIC TOFA-20, tall oil fatty acid ethoxylate, HLB=14.8, Huntsman Petrochemical Corp., Salt Lake City, Utah; and poly $C_2$–$C_4$ alkylene glycol mono- $C_{10}$–$C_{20}$ alkyl ethers, e.g., $C_{11\text{-}15}$ PARETH-20 and CETEARETH-55, HLB=24.

In a preferred embodiment of the invention, both the icons and the gel matrix material are prepared from water; KELCOGEL® F gellan gum, a low acyl clarified product of the Monsanto Company of St. Louis, Mo.; methylchloroisothiazolinone; methylisothiazolineone; propylene glycol; ethyl alcohol; nonoxynol-15, in the case of the gel matrix air freshener article body; nonoxynol-4, in the case of gel matrix air freshener article icon; potassium citrate; fragrance composition, the components of which have an average $C\log_{10}P=2.5$, in the case of the gel matrix air freshener article body; and fragrance composition, the components of which have an average $C\log_{10}P=4.5$ in the case of the gel matrix air freshener article icon. Pigment is added to the icon material in an amount effective for making the icon material opaque and then the material is molded to form icons. The icons are placed in ajar and frozen. Hot gel matrix material is poured over the frozen icons to provide a gel air freshener having included icons that shrink in proportion to the gel matrix material.

The water that is used to prepare both the icons and the gel matrix material is preferably deionized water or distilled water and is used in an amount between about 50% and about 90% by weight of the composition, preferably in an amount between about 70% and about 85% by weight, most preferably in an amount between about 75% and about 80%.

Preferred gel matrix polysaccharide materials useful in the practice of our invention are gellan gums, e.g., KELCOGEL® LT-100 a high acyl unclarified product, KELCOGEL® LT a low acyl unclarified product, KELCOGEL® F a low acyl clarified product and KELCOGEL® AFT produced by the KELCO Biopolymer Division of the Monsanto Company, Chicago, Ill. Such gellan gum is, most preferably, formed by inoculating a fermentation medium having, as a substrate, glucose, with the microorganism *Sphingomonas elodea* followed by de-acetylation and alcoholic precipitation. The gellan gum is used in an amount between about 0.1% and about 10% by weight of the composition, preferably in an amount between about 0.5% and about 2% by weight, most preferably in an amount of about 1% by weight. In one embodiment of the invention, the icons have a higher concentration of gellan gum than the surrounding matrix.

The most preferable antimicrobial agents used in the practice of our invention are methylchloroisothiazolinone and methylisothiazolineone that are marketed in combination under the trademark KATHON® CG by Rohm and Haas Co., Philadelphia, Pa. As stated herein, they are optionally present in the composition and can be used in an amount between about 0.001% and about 7.0% by weight of the composition, preferably in amount between about 0.01% and about 1.0% by weight, most preferably in amount of about 0.03% by weight.

When a $C_2$–$C_6$ alkylene glycol is contained in the gel matrix air freshener body or in the gel matrix icon, the preferred alkylene glycol is propylene glycol. When it is used, the propylene glycol is used in an amount between about 0.5% and about 20% by weight of the composition, preferably in an amount between about 1% and about 10% by weight, most preferably in an amount of about 4% by weight.

Optionally the gel matrix air freshener body and/or the gel matrix icon can contain a lower alkanol such as ethanol. A preferred lower alkanol useful in this context is 190 proof ethanol and, when used, is used in an amount between about 0.1% and about 20% by weight of the composition, preferably in an amount between about 1% and about 5% by weight, and most preferably in an amount of about 3% by weight. Alternatively, other lower alkanols such as methanol, propanol, isopropanol, and the like can be used.

In the gel matrix air freshener body of the air freshener article, a preferred surfactant is nonoxynol-15 o-(hydroxy (ethoxy)$_{15}$))nonylphenyl ether; or "PEG-15 nonylphenyl ether" which is marketed under the trademark IGEPAL® CO730 by Rhodia, Inc., Cranbury, N.J. The surfactant is used in an amount between about 0.1% and about 25% by weight of the composition, preferably in an amount between about 1% and about 20% by weight, most preferably in an amount of between about 5% and about 15% by weight. The nonoxynol-15 is a non-ionic surfactant and the amount that is required is dependent on the character of the particular fragrance that is used.

By the same token, in the practice of our invention in the gel matrix air freshener icon of the air freshener article of our invention, a preferred surfactant, which is optional in the case of the presence thereof in the icon, is nonoxynol-4, o-(hydroxy(ethoxy)$_4$) nonylphenyl ether; or PEG-4 nonylphenyl ether which is marketed under the trademark IGEPAL® CO430 by Rhodia, Inc., Cranbury, N.J. When used, it is used in an amount between about 0.1% and 25% by weight of the icon composition, preferably in an amount between about 1% and 20% by weight, most preferably in an amount of between about 5% and 15% by weight. The nonoxynol-4 is a non-ionic surfactant and the amount that is required is dependent on the character of the particular fragrance that is used.

When chelating agents are used in the air freshener body and in the gel matrix icon(s) of our invention, the most preferred chelating agent is tri-potassium citrate. When used, it is used in amount between about 0.05% and 4.0% by weight of the composition, preferably in an amount between about 0.1% and 1% by weight, most preferably in an amount of about 0.2% by weight.

A preferred embodiment of the process of our invention comprises the steps of:

(a) admixing the clear gel matrix material, e.g., the gellan gum, with water at a temperature in the range of from about 65° C. up to about 80° C. to form an aqueous gel matrix solution;

(b) dividing the resulting solution into two portions: (i) an icon portion; and (ii) a body portion, the volume fraction $\phi$ of the icon portion being $\phi = V_I'/(V_o'+V_I')$; wherein $0.01 \leq \phi \leq 0.90$ and wherein $V_I'$ is the volume of the "icon" portion and $V_o'$ is the volume of the body portion;

(c) maintaining the body portion in the liquid state at a temperature of from about 65° C. up to about 80° C.

(d) pouring the icon portion into one or more icon molds;

(e) optionally adding one or more of the same or different pigments as set forth in Examples 1–9, herein, to one or more of the icon molds containing the icon portion while the icon portion is in the liquid state;

(f) cooling the icon portion to a temperature below the solidification temperature of the icon portion whereby one or more icons in the solid state are formed;

(g) removing the one or more icons in the solid state from the one or more icon molds;

(h) permanently submerging the entirety of the one or more icons in the body portion whereby the one or more frozen icons is suspended in the body portion; and (i) within a time period sufficiently short in length to prevent the melting of the one or more suspended icons, cooling the resulting suspension to a temperature in the range of from about 10° C. up to about 30° C., whereby the resulting suspension is transformed to the solid or semi-solid phase.

More specifically, and by way of example, to prepare the gel matrix icon and gel matrix air freshener article body material, the water is added to a steam-jacketed vessel with a mechanical stirrer. The gellan gum is sprinkled into the vortex and heated to about 70° C. Once the mixture is completely clear, the heat is removed and the aqueous gellan gum solution is cooled to about 60° C. Then the remaining ingredients are added with stirring.

The icons are prepared by pouring the hot formula into molds and permitting the formula to solidify. While the formula is maintained in a hot liquid state, pigment is added to the icon material in an amount effective for rendering the icon visually distinct from the surrounding gel matrix. Suitable pigments include, but are not limited to, iron oxide yellow, iron oxide cosmetic russet, cloisonne super rouge, cloisonne super rouge with polyflake, graphtol blue powder, graphtol green powder, titanium dioxide, and mixtures of the pigments. The icon is then removed from the mold, in a solidified state, and positioned in an air freshener container. The gel matrix air freshener article body material is poured into the container having the solidified icons therein and allowed to solidify to room temperature before being capped.

When each of the gel matrix icons and the gel matrix air freshener body of the air freshener article of our invention contains a system-compatible air freshener fragrance composition prior to use of the gel matrix air freshener article of our invention, the operation of the gel matrix air freshener article of our invention is in accordance with the algorithm:

$$\int\{(v_I[\partial c_I/\partial\theta]-V_o[\partial c_o/\partial\theta]+c_I[\partial V_I/\partial\theta]-c_o[\partial V_o/\partial\theta])d\theta\}=k_1\Delta(c_oV_o)+(1-\phi)\int\int[\partial E_o/\partial V_o]dV_od\theta+\phi\int\int[\partial E_I/\partial V_I]dV_Id\theta$$

wherein $V_1$ is the total volume of the icons at time $\theta$;

wherein $V_o$ is the total air freshener body volume at time $\theta$;

wherein $c_I$ is the average perfume composition component concentration in gram-moles per liter in all of the icons at time $\theta$;

wherein $c_o$ is the average perfume composition component concentration in gram-moles per liter in the air-freshener body at time $\theta$;

wherein $E_o$ is the elastic modulus of the air freshener body at time $\theta$;

wherein $E_I$ is the average elastic modulus of each of the icons at time $\theta$;

wherein $k_I$ is a constant; and wherein $\phi$ is the volume fraction of the icons;

or the algorithm:

$$\Delta(V_o^{-1/2})+\Delta(V_I^{-1/2})-\Delta(\ln c_I)-\Delta(\ln c_o)=-k_2(\Delta\theta)$$

wherein $V_I$ is the total volume of the icons at time $\theta$;

wherein $V_o$ is the total air freshener body volume;

wherein $c_I$ is the average perfume composition component concentration in gram-moles per liter in all of the icons at time $\theta$;

wherein $c_o$ is the average perfume composition component concentration in gram-moles per liter in the air freshener body at time $\theta$; and wherein $k_2$ is a constant;

or the algorithm:

$$(c_{I2}c_{o2})/(c_{I1}c_{o1})=exp[k_2\Delta\theta+\Delta(V_o^{-1/2})+\Delta(V_I^{-1/2})]$$

wherein $V_I$ is the total volume of the icons at time $\theta$;

wherein $V_o$ is the total air freshener body volume at time $\theta$;

wherein $c_{I1}$ is the average perfume composition component concentration in gram-moles per liter in all of the icons at time $\theta_1$;

wherein $c_{I2}$ is the average perfume composition component concentration in gram-moles per liter in all of the icons at time $\theta_2$;

wherein $C_{o1}$ is the average perfume composition component concentration in gram-moles per liter in the air freshener body at time $\theta_1$;

wherein $c_{o2}$ is the average perfume composition component concentration in gram-moles per liter in the air freshener body at time $\theta_2$; and wherein $k_2$ is a constant.

The following non-limiting examples are presented for purposes of illustration. All fragrance materials set forth in the examples are available from International Flavors & Fragrances Inc., Hazlet, N. J.

EXAMPLE A

Preparation of Air Freshener Fragrance for Gel Matrix Air Freshener Article Body The following fragrance is prepared for use in Part "A" of EXAMPLES 1–9, infra:

| Ingredients | Parts by Weight |
| --- | --- |
| α-Irone | 7.0 |
| Myristicin | 4.0 |
| 2-Methoxynaphthalene | 3.0 |
| Benzaldehyde | 2.0 |
| β-Phenylethyl alcohol | 12.0 |
| Nerol | 7.0 |
| Eugenol | 8.0 |
| Isoeugenol | 2.0 |

EXAMPLE B

Preparation of Air Freshener Fragrance for Gel Matrix Air Freshener Article Icon(s)

The following fragrance was prepared for use in Part "B" of Examples 1–9, infra:

| Ingredients | Parts by Weight |
| --- | --- |
| Amyl salicylate | 4.0 |
| β-Caryophyllene | 14.0 |
| Cedryl acetate | 16.0 |
| Cyclohexyl salicylate | 4.0 |
| γ-Dodecalactone | 3.0 |
| Geranyl anthranilate | 3.0 |
| α-Irone | 10.0 |

EXAMPLES 1–9

PART A: A gel matrix air freshener article body gel matrix material was prepared by adding 76.77% by weight deionized water to a steam-jacketed vessel with a mechanical stirrer. The stirrer was turned on and 1.00% by weight KELCOGEL® AFT gellan gum, Monsanto Company of St. Louis, Mo., was sprinkled into the vortex and heated to about 70° C. Once the aqueous gellan gum solution was completely clear, it was permitted to cool.

Three one-hundredths percent 0.03% by weight KATHON® CG (Rohm and Haas Co., Philadelphia, Pa.); 4.0% by weight propylene glycol; 3.00% by weight ethanol in water, 190 proof, 10.00% by weight IGEPAL® CO730, Rhone-Poulenc Surfactants and Specialties L.P., Cranbury, N.J., also known as nonoxynol-15 or PEG-15 nonylphenyl ether, 0.02% by weight potassium citrate, and 5.00% by weight of the fragrance formulation of EXAMPLE A, supra, were added to the gellan gum solution with stirring when the solution reached 60° C.

PART B: A gel matrix air freshener article icon gel matrix material was prepared by adding 76.77% by weight deionized water to a steam-jacketed vessel with a mechanical stirrer. The stirrer was turned on and 1.00% by weight KELCOGEL® AFT gellan gum was sprinkled into the vortex and heated to about 70° C. Once the aqueous gellan gum solution was completely clear, it was permitted to cool.

Three one-hundredths percent 0.03% by weight KATHON® CG; 4.0% by weight propylene glycol; 3.00% by weight ethanol in water, 190 proof; 10.00% by weight IGEPAL® CO430, also known as nonoxynol-4 or PEG-4 nonylphenyl ether, 0.02% by weight potassium citrate, and 5.00% by weight of the fragrance formulation of EXAMPLE B, supra, were added to the gellan gum solution with stirring when the solution reached 60° C.

Pigments were added to separate portions of the material in an amount effective to render the material opaque. The following pigments were used:

1. Iron oxide yellow from Sun Chemical;
2. Iron oxide cosmetic russet from Sun Chemical;
3. Iron oxide cosmetic russet with titanium dioxide;
4. Cloisonne super rouge;
5. Cloisonne super rouge with polyflake (polyester glitter);
6. Cloisonne super red;
7. Graphic blue powder;
8. Titanium dioxide; and
9. Lake pigments.

Each portion of individually colored material was molded into the form of a cube and frozen.

Clear gel matrix material prepared according to Part A was poured over each of the colored cubes. After three (3) days, all of the cubes maintained their form without any migration of pigment with the exception of the cube #6 containing cloisonne super red. In that instance, a very slight haze was observed at the edge of the cube.

The resulting gel matrix clear air freshener articles, on use provided aestheticlly pleasing rose, woody aromas with sweet floral balsamic topnotes and orris, violet-like undertones.

EXAMPLE 10

Seven (7) icons containing cloisonne super rouge and seven icons containing titanium dioxide were prepared as described in connection with Examples 1–9, except that the icons were molded in the form of a heart. The icons were placed in a jelly jar and the jar was filled with clear base material. The icons maintained their form after three days.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A substantially rigid aqueous clear gel matrix air freshener article consisting essentially of:
   (a) an air freshener gel matrix body which is a single body having a volume $V_o$ which decreases on use of said air freshener article whereby $dV_o/d\theta<0$ comprising (i) about 50–90% by weight of water, (ii) about 0.1–25% by weight of a surfactant having a hydrophile/lipophile balance in the range of from about 10 to about 30, (iii) about 0.1–10% by weight of a clear gel matrix material selected from the group consisting of a polysaccharide gel matrix material and a hydrolyzed protein gel matrix material, (iv) a non-gelling hydrocolloid (v) about 0.1–20% by weight of a system-compatible air freshening fragrance composition, each of the components of which has a C $\log_{10}P$ of from about 1 to about 4 and the components of which have an average C $\log_{10}P$ of about 2.5, wherein P is the octanol/water partition coefficient for each of the fragrance components, (vi) about 0.1–20% by weight of a lower alkanol, (vii) about 0.001–7% by weight of an antimicrobial agent, (viii) about 0.5–20% by weight of a $C_2$–$C_6$ alkylene glycol, and (ix) about 0.05–4.0% by weight of a chelating agent;
   (b) fully imbedded within said air freshener body, one or more molded gel matrix icons which are each permanently visibly distinct from said gel matrix body over the range of visible wavelengths when contained within said air freshener gel matrix body, the total volume of which is $V_1$ which decreases on use of said air freshener article whereby $dV_1/d\theta<0$ each of which icon comprises (i) about 50–90% by weight of water, (ii) about 0.1–10% by weight of a clear gel matrix material selected from the group consisting of a polysaccharide gel matrix material and a hydrolyzed protein gel matrix material, (iii) about 0.1–20% by weight of a system-compatible air freshening fragrance composition each of the components of which has a C $\log_{10}P$ of from about 1 to about 8 and the components of which have an average C $\log_{10}P$ of about 4.5, wherein P is the octanol/water partition coefficient for each of the fragrance components, (iv) an opacifying agent which is a pigment, (v) a non-gelling hydrocolloid, (vi) about 0.1–25% by weight of a surfactant having a hydrophile/lipophile balance of less than about 10, (vii) about 0.1–20% by weight of a lower alkanol, (viii) about 0.001–7% by weight of an antimicrobial agent, (ix) about 0.5–20% by weight of a $C_2$–$C_6$ alkylene glycol, and (x) about 0.05–4.0% by weight of a chelating agent;

with the volume fraction of said icons in said air freshener article being $\phi=V_I/(V_I+V_o)$ wherein $0.01 \leq \phi \leq 0.90$, the physical and chemical properties of each of said icons and said air freshener body being such that on use of said air freshener article, (i) the rate of volumetric reduction of each of said icons as a result of fragrance emission and water emission therefrom with respect to the volumetric reduction of the air freshener body which envelops said icons as a result of fragrance emission and water emission therefrom is a constant, according to the equations: $\partial V_I/\partial V_o=\phi/(1-\phi)$ and $\partial^2 V_I/\partial V_o^2=0$, (ii) the integrity of the fragrance compositions emitted from said air freshener body and said icons is maintained and (iii) the distinguishing visibility of the icons in said air freshener body from without said air freshener body, at visible wavelengths, is maintained.

2. The air freshener article of claim 1 wherein the air freshener body additionally comprises at least one additive selected from the group consisting of an anti-oxidant and a $C_2$–$C_6$ (mono- or di-) alkylene glycol-$C_2$–$C_4$ alkyl ether.

3. The air freshener article of claim 2 wherein the icons additionally comprise at least one additive selected from the group consisting of an anti-oxidant and a $C_2$–$C_6$ (mono- or di-) alkylene glycol mono-$C_2$–$C_4$ alkyl ether.

4. The air freshener article of claim 1 wherein the clear gel matrix material is a polysaccharide and the polysaccharide is selected from the group consisting of gellan gum, alkali metal salts of alginic acid, alkaline earth metal salts of alginic acid, and carageenan.

5. The air freshener article of claim 1 wherein the clear gel matrix material is a hydrolyzed protein gel matrix which is gelatin having an isoelectric point of from about 4 up to about 7.

6. The air freshener article of claim 3 wherein the antimicrobial agent is selected from the group consisting of potassium dimethyldithiocarbamate, glutaraldehyde, 2-bromo-2-nitropropane-1,3-diol, o-phenyl phenol, 1-(3-chloroallyl)-3,5,7-triaza-1-azoniaadamantane chloride, N,N'-dimethyl-5,5-dimethoxy-2,4-imidazolidinedione, methylchloroisothiazolinone and methylisothiazolinone; the chelating agent is selected from the group consisting of an alkali metal salt of citric acid, an ammonium salt of citric acid, an alkali metal salt of ethylenediamine tetraacetic acid, an ammonium salt of ethylene diamine tetraacetic acid, an alkali metal salt of N-hydroxyethylenediamine triacetic acid, an ammonium salt of N-hydroxyethylene-diaminetriacetic acid, an alkali metal salt of iminodisuccinic acid, an ammonium salt of iminodisuccinic acid, an alkali metal salt of ethylenediamine disuccinic acid and an ammonium salt of ethylene diamine disuccinic acid; the $C_2$–$C_6$ alkylene glycol is 1,2-propylene glycol; and the $C_2$–$C_6$ (mono- or di-) alkylene glycol $C_2$–$C_4$ alkyl ether is dipropylene glycol-n-butyl ether.

7. The air freshener article of claim 1 wherein the air freshener body is fully surrounded by a clear substantially solid or semi-solid microporous boundary surface permitting passage of water molecules and fragrance composition component molecules therethrough on use of said article.

8. The air freshener article of claim 1 supported by means of an external support comprising a solid base having vertically-disposed solid sidewalls extending therefrom.

9. The air freshener article of claim 1 wherein the surfactant contained in the gel matrix air freshener body is selected from the group consisting of poly ($C_2$–$C_4$ alkylene glycol)$_{6-30}$ mono ([$C_8$–$C_{10}$ alkyl]phenyl)ethers; 1,Ω-poly $C_2$–$C_4$ alkylene glycols; poly $C_2$–$C_4$ alkylene glycol mono-$C_{10}$–$C_{20}$ alkanoic acid esters; poly $C_2$–$C_4$ alkylene glycol sorbitan mono-$C_{10}$–$C_{20}$ alkanoic acid esters; poly $C_2$–$C_4$ alkylene glycol tallow amines; poly $C_2$–$C_4$ alkylene glycol esters of tall oil fatty acids; and poly $C_2$–$C_4$ alkylene glycol mono-$C_{10}$–$C_{20}$ alkyl ethers.

10. The air freshener article of claim 1 wherein the opacifying pigment contained in the icons is selected from the group consisting of iron oxide yellow, iron oxide cosmetic russet, cloisonne super rouge, cloisonne super rouge with polyflake, graphtol blue powder, graphtol green powder, titanium dioxide and Lake colors.

11. The air freshener article of claim 1 wherein the weight percent of water in said article is from about 75–80% by weight of said article; the weight percent of clear gel matrix material is from about 0.5–2% by weight of said article; the weight percent of system-compatible fragrance in said article is from about 1–10% by weight of said article and the weight percent of surfactant in said article is from about 5–15% by weight of said article.

12. The air freshener article of claim 1 wherein on use of said article, the operation of the air freshener article is in accordance with the algorithm:

$$\int\{(v_I[\partial c_I/\partial\theta]-V_o[\partial c_o/\partial\theta]+c_I[\partial V_I/\partial\theta]-c_o[\partial V_o/\partial\theta])d\theta\}=k_1\Delta(c_oV_o)+(1-\phi)\int\int\{\partial E_o/\partial V_o\}dV_od\theta+\phi\int\int\{\partial E_I/\partial V_I\}dV_Id\theta$$

wherein $V_I$ is the total volume of the icons at time $\theta$;

wherein $V_o$ is the air freshener body volume at time $\theta$;

wherein $c_I$ is the average perfume composition component concentration in gram-moles per liter in all of the icons at time $\theta$;

wherein $c_o$ is the average perfume composition component concentration in gram-moles per liter in the air-freshener body at time $\theta$;

wherein $E_o$ is the elastic modulus of the air freshener body at time $\theta$;

wherein $E_I$ is the average elastic modulus of each of the icons at time $\theta$;

wherein $k_I$ is a constant; and wherein $\phi$ is the volume fraction of the icons.

13. The air freshener article of claim 1 wherein on use of said article, the operation of the air freshener article is in accordance with the algorithm:

$$\Delta(V_o^{-1/2})+\Delta(V_I^{-1/2})-\Delta(\ln c_I)-\Delta(\ln c_o)=-k_2(\Delta\theta)$$

wherein $V_I$ is the total volume of the icons at time $\theta$;

wherein $V_o$ is the air freshener body volume;

wherein $C_1$ is the average perfume composition component concentration in gram-moles per liter in all of the icons at time $\theta$;

wherein $C_o$ is the average perfume composition component concentration in gram-moles per liter in the air freshener body at time $\theta$; and wherein $k_2$ is a constant.

14. The air freshener article of claim 1 wherein on use of said article, the operation of the air freshener article is in accordance with the algorithm:

$$(c_{I2}c_{o2})/(c_{I1}c_{o1})=\exp[k_2\Delta\theta+\Delta(V_o^{-1/2})+\Delta(V_I^{-1/2})]$$

wherein $V_I$ is the total volume of the icons at time $\theta$;

wherein $V_o$ is the total air freshener body volume at time $\theta$;

wherein $c_{I1}$ is the average perfume composition component concentration in gram-moles per liter in all of the icons at time $\theta_I$;

wherein $c_{I2}$ is the average perfume composition component concentration in gram-moles per liter in all of the icons at time $\theta_2$;

wherein $c_{oI}$ is the average perfume composition component concentration in gram-moles per liter in the air freshener body at time $\theta_I$;

wherein $c_{o2}$ is the average perfume composition component concentration in gram-moles per liter in the air freshener body at time $\theta_2$; and wherein $k_2$ is a constant.

15. The process for preparing the air freshener article of claim 1 comprising the steps of:

(a) admixing the clear gel matrix material with water at a temperature in the range of from about 65° C. up to about 80° C. to form an aqueous gel matrix solution;

(b) dividing the resulting solution into two portions: (i) an "icon" portion; and (ii) a "body" portion, the volume fraction $\phi$ of the "icon" portion being $\phi = V_I'/(V_o' + V_I')$; wherein $0.01 \leq \phi 0.90$ and wherein $V_I'$ is the volume of the "icon" portion and $V_o'$ is the volume of the "body" portion;

(c) maintaining the "body" portion in the liquid state at a temperature of from about 65° C. up to about 80° C.;

(d) pouring the "icon" portion into one or more icon molds;

(e) adding an opacifying quantity of one or more of the same or different pigments to one or more of the icon molds containing the "icon" portion while the "icon" portion is in the liquid state;

(f) cooling the "icon" portion to a temperature below the solidification temperature of the "icon" portion whereby one or more frozen icons in the solid state are formed;

(g) removing the one or more frozen icons in the solid state from the one or more icon molds;

(h) permanently submerging the entirety of the one or more frozen icons in the "body" portion whereby the one or more frozen icons is suspended in the "body" portion; and (i) within a time period sufficiently short in length to prevent the melting of the one or more suspended icons, cooling the resulting suspension to a temperature in the range of from about 10° C. up to about 30° C. whereby the resulting suspension is transformed to the solid or semi-solid phase.

16. The air freshener article of claim 4 wherein the clear gel matrix material is gellan gum and each of the icons has a higher concentration of gellan gum than the surrounding matrix.

17. The air freshener article of claim 1 wherein each of the icons is in the form of a cube.

18. The air freshener article of claim 15 wherein each of the icons is in the form of a cube.

* * * * *